United States Patent
Hibner

(10) Patent No.: US 10,149,726 B2
(45) Date of Patent: Dec. 11, 2018

(54) METHODS, SYSTEMS, AND DEVICES FOR INITIALIZING A SURGICAL TOOL

(71) Applicant: Ethicon Endo-Surgery, LLC, Guaynabo, PR (US)

(72) Inventor: John A. Hibner, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 158 days.

(21) Appl. No.: 15/200,283

(22) Filed: Jul. 1, 2016

(65) Prior Publication Data

US 2018/0000543 A1 Jan. 4, 2018

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/20* (2016.02); *A61B 34/71* (2016.02); *A61B 17/068* (2013.01);
(Continued)

(58) Field of Classification Search
CPC ......... A61B 34/30; A61B 34/20; A61B 34/71; A61B 17/28; A61B 17/2804; A61B 17/2812; A61B 17/2816; A61B 17/282; A61B 17/2833; A61B 17/29; A61B 2017/2808; A61B 2017/2837; A61B 2017/2901; A61B 2017/2902; A61B 2017/2908; A61B 2017/2926; A61B 2017/2927; A61B 2017/2931;
(Continued)

(56) References Cited

U.S. PATENT DOCUMENTS 8,771,270 B2 7/2014 Burbank
8,831,782 B2 9/2014 Itkowitz
(Continued)

FOREIGN PATENT DOCUMENTS

WO WO-2014151621 A1 9/2014
WO WO-2014151952 A1 9/2014
WO WO-2015125914 A1 8/2015

OTHER PUBLICATIONS

International Search Report for PCT/US2017/035912 dated Sep. 27, 2017 (9 pages).

*Primary Examiner* — Eric Rosen
*Assistant Examiner* — Chima Igboko
(74) *Attorney, Agent, or Firm* — Mintz Levin/EES

(57) ABSTRACT

Various exemplary methods, systems, and devices for initializing a surgical tool are provided. In general, a surgical tool can include an end effector, an elongate shaft, and a wrist that couples the end effector to a distal end of the shaft. The wrist can be configured to facilitate movement of the end effector relative to the shaft. The surgical tool can include multiple flexible members configured to move, either individually or as a group including any plural number of the flexible members, to cause the movement of the end effector relative to the shaft by pivoting at the wrist. The movement of the end effector can include movement between an unarticulated position and an articulated position. The surgical tool can also include one or more homing members configured to be selectively actuated to force the end effector into the unarticulated position.

21 Claims, 14 Drawing Sheets

(51) Int. Cl.
*A61B 34/20* (2016.01)
*A61B 17/29* (2006.01)
*A61B 17/068* (2006.01)
*A61B 17/10* (2006.01)
*A61B 17/3201* (2006.01)
*A61B 18/14* (2006.01)

(52) U.S. Cl.
CPC .............. *A61B 17/10* (2013.01); *A61B 17/29* (2013.01); *A61B 17/3201* (2013.01); *A61B 18/1445* (2013.01); *A61B 2017/2908* (2013.01); *A61B 2017/2927* (2013.01); *A61B 2034/2059* (2016.02); *A61B 2034/305* (2016.02); *A61B 2034/306* (2016.02); *A61B 2034/715* (2016.02); *A61B 2217/005* (2013.01); *A61B 2217/007* (2013.01)

(58) Field of Classification Search
CPC .... A61B 2017/2932; A61B 2017/2933; A61B 2017/2934; A61B 2017/2936; A61B 2017/2937; A61B 2017/2939; A61B 2017/294; A61B 2017/2941; A61B 2017/2946; A61B 18/085; A61B 18/1442; A61B 18/1445; A61B 2018/0225; A61B 10/06

See application file for complete search history.

(56) References Cited

U.S. PATENT DOCUMENTS

| | | |
|---|---|---|
| 9,055,961 B2 | 6/2015 | Manzo et al. |
| 2004/0236316 A1* | 11/2004 | Danitz ................. A61B 1/0055 606/1 |
| 2009/0202387 A1 | 8/2009 | Dlugos, Jr. et al. |
| 2014/0005640 A1* | 1/2014 | Shelton, IV ....... A61B 18/1442 606/1 |
| 2015/0094737 A1 | 4/2015 | Hatakeyama |
| 2016/0213224 A1* | 7/2016 | Hatakeyama .............. B25J 3/04 |
| 2016/0374772 A1 | 12/2016 | Hasegawa et al. |

* cited by examiner

METHODS, SYSTEMS, AND DEVICES FOR INITIALIZING A SURGICAL TOOL

FIELD

The present disclosure relates generally to methods, systems, and devices for initializing a surgical tool.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining natural eye-hand axis. Robotic systems can also allow for more degrees of freedom in movement by including a "wrist" joint on the instrument, creating a more natural hand-like articulation. One drawback with robotic systems, however, is that a starting position of the "wrist" joint changes over time due to the flexing of flexible components used for articulation that over time creates some degree of slack in the flexible components. The articulation thus becomes less precisely controlled over time, resulting in the instrument not being positioned as precisely as desired.

Accordingly, there remains a need for improved methods, systems, and devices for initializing a surgical tool.

SUMMARY

In general, methods, systems, and devices for initializing a surgical tool are provided.

In one aspect, a surgical tool is provided that in one embodiment includes a tool shaft, an end effector coupled to a distal end of the tool shaft, a multi-axial wrist disposed between the tool shaft and the end effector, a plurality of flexible cables extending along the tool shaft and operatively coupled to the end effector such that tension selectively applied to one or more of the plurality of flexible cables causes at least one of pitch and yaw motion of the end effector, and a homing rod configured to be selectively moveable relative to the end effector for forcing the end effector into a substantially zero-angle position relative to the tool shaft.

The surgical tool can vary in any number of ways. For example, the end effector can include first and second jaws, and the homing rod can be configured to extend into a recess formed in the first jaw. For another example, the end effector can include first and second jaws, and the homing rod can include first and second rods, the first rod being configured to extend into a first recess formed in the first jaw, and the second rod being configured to extend into a second recess formed in the second jaw. For yet another example, the homing rod can be configured to extend through a bore in the multi-axial wrist to prevent motion of the multi-axial wrist. For still another example, the end effector can include first and second jaws, and the plurality of flexible cables can be configured to move the first and second jaws between open and closed positions. For another example, the surgical tool can include a housing coupled to a proximal end of the end effector, and the housing can be configured to couple to a driver of a surgical robot such that the driver can control movement of the plurality of flexible cables. For another example, the homing rod forcing the end effector in the substantially zero-angle position can prevent the end effector from moving from the substantially zero-angle position to a non-zero angle position. For yet another example, the surgical tool can include a plurality of sensors configured to sense a position of each of the plurality of flexible cables when the end effector is in the substantially zero-angle position. For still another example, the movement of the homing rod can be independent of the movement of the plurality of flexible cables. For another example, the movement of the plurality of flexible cables can be in a proximal direction, and the movement of the rigid rod can be in a distal direction.

In another embodiment, a surgical tool is provided that includes a housing having a plurality of inputs configured to couple to at least one motor on a tool driver of a surgical robot, an elongate shaft extending from the housing, an end effector coupled to a distal end of the elongate shaft and pivotally movable about at least one pivot joint formed between the end effector and the elongate shaft, and a plurality of flexible cables coupled to the plurality of inputs in the housing, extending along the elongate shaft, and operatively coupled to the end effector. Proximal movement of the plurality of flexible cables is effective to cause pivotal movement of at least a portion of the end effector relative to the elongate shaft. The surgical tool also includes a rigid member operably associated with the end effector and configured to be selectively advanced into the end effector to force the end effector into substantial longitudinal alignment with the elongate shaft.

The surgical tool can vary in any number of ways. For example, the surgical tool can include a first actuator configured to be actuated to advance the rigid member into the end effector. The first actuator can include a rotating member configured to rotate to longitudinally translate the rigid member to advance the rigid member into the end effector, and/or the surgical tool can include a second actuator configured to be actuated to pull the plurality of flexible cables proximally to move the plurality of flexible cables relative to the elongate shaft to pivot at least the portion of the end effector relative to the elongate shaft.

For another example, each of the plurality of flexible cables can be configured to move proximally relative to the elongate shaft to pivot the end effector relative to the elongate shaft, and the rigid member can be configured to move distally relative to the elongate shaft to force the substantial longitudinal alignment of the end effector with the elongate shaft.

For yet another example, the end effector can include a pair of jaws, and the plurality of flexible cables can be configured to move relative to the elongate shaft to selectively open and close the pair of jaws. The rigid member can include a pair of rigid members, and each of the rigid members can be configured to be advanced into one of the jaws.

For still another example, the end effector can include one of forceps, graspers, a needle driver, scissors, an electrocautery tool, a stapler, a clip applier, a suction tool, and an irrigation tool.

For another example, the surgical tool can include a plurality of sensors configured to sense a position of each of the plurality of flexible cables when the rigid member is advanced into the end effector and the end effector is substantially longitudinally aligned with the elongate shaft. The surgical robot can include a memory and a controller, and the controller can be configured to cause the sensed position of each of the plurality of flexible cables to be stored in the memory. The controller can be configured to receive a user-initiated input requesting movement of the end effector relative to the elongate shaft and to cause the requested movement by causing one or more of the plurality of flexible cables to move relative to the elongate shaft with reference to the stored sensed position of each of the plurality of flexible cables, and/or the controller can be configured to cause the plurality of flexible cables to be tensioned prior to the sensing of the position of each of the plurality of flexible cables with the plurality of sensors sensing the position of the plurality of flexible cables when the plurality of flexible cables are tensioned.

In another aspect, a surgical system is provided that in one embodiment includes a surgical tool, a memory, and a controller. The surgical tool includes a tool shaft, an end effector coupled to a distal end of the tool shaft, a multi-axial wrist disposed between the tool shaft and the end effector, a plurality of flexible cables extending along the tool shaft and operatively coupled to the end effector such that tension selectively applied to one or more of the plurality of flexible cables causes at least a portion of the end effector to rotate about at least one axis of the multi-axial wrist, a rigid rod configured to be selectively moved relative to the end effector to force the end effector into a substantially zero-angle position relative to the tool shaft, and a plurality of sensors configured to sense a position of each of the plurality of flexible cables when the end effector is in the substantially zero-angle position. The controller is configured to cause the sensed position of each of the plurality of flexible cables to be stored in the memory.

The surgical system can vary in any number of ways. For example, the controller can be configured to receive a user-initiated input requesting movement of the end effector relative to the tool shaft and to cause the requested movement by causing one or more of the plurality of flexible cables to move relative to the tool shaft with reference to the stored sensed position of each of the plurality of flexible cables. For another example, the controller can be configured to cause the plurality of flexible cables to be tensioned prior to the sensing of the position of each of the plurality of flexible cables, the plurality of sensors sensing the position of each of the plurality of flexible cables when the plurality of flexible cables are tensioned.

In another aspect, a surgical method is provided that in one embodiment includes actuating a surgical robot to cause a rigid rod to force an end effector into a substantially longitudinally aligned position with a shaft coupled to the end effector, and with the end effector in the substantially longitudinally aligned position, actuating the surgical robot to tension one or more of the plurality of flexible cables and sensing a position of a plurality of flexible cables coupled to the end effector. The sensed position of the plurality of flexible cables defines a home position of the end effector. The surgical method also includes actuating the surgical robot to tension one or more of the plurality of flexible cables to cause at least a portion of the end effector to pivot relative to the shaft about at least one pivot joint formed between the end effector and the shaft.

The surgical method can have any number of variations. For example, the rigid rod forcing the end effector into the substantially longitudinally aligned position can prevent the end effector from pivoting relative to the shaft, and the surgical method can include actuating the surgical robot to release the rigid rod's forcing of the end effector into the substantially longitudinally aligned position and thereby allow the end effector to pivot from the substantially longitudinally aligned position. For another example, forcing the end effector into the substantially longitudinally aligned position can include distally advancing the rigid rod from the shaft into the end effector. For yet another example, the surgical method can include receiving at the surgical robot a user-initiated input requesting movement of the end effector relative to the shaft, and causing the requested movement by causing one or more of the plurality of flexible cables to move relative to the shaft with reference to the home position of the end effector. For still another example, actuating the surgical robot to cause the rigid rod to force the end effector into the substantially longitudinally aligned position, the sensing, and actuating the surgical robot to tension the one or more of the plurality of flexible cables can occur during a first surgical procedure being performed on a first patient, and the surgical method can include performing, during a second surgical procedure being performed on a second patient, actuating the surgical robot to cause the rigid rod to force the end effector into the substantially longitudinally aligned position, and sensing a second position of the plurality of flexible cables coupled to the end effector with the end effector in the substantially longitudinally aligned position, the sensed second position of the plurality of flexible cables defining a new home position of the end effector.

BRIEF DESCRIPTION OF DRAWINGS

This invention will be more fully understood from the following detailed description taken in conjunction with the accompanying drawings, in which.

DETAILED DESCRIPTION

Figure 1:
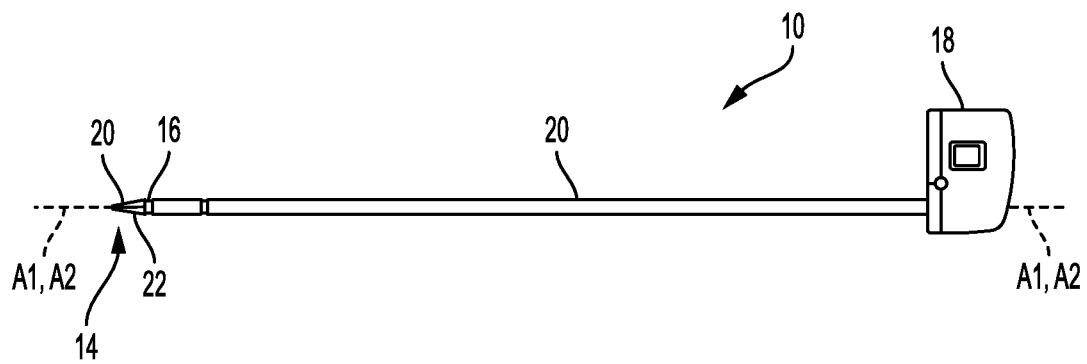
FIG. 1 is a side schematic view of one embodiment of a surgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

Various exemplary methods, systems, and devices for initializing or resetting a surgical tool are provided. In general, a surgical tool can include an elongate shaft and a wrist that couples an end effector to a distal end of the shaft. The wrist can be configured to facilitate movement of the end effector relative to the shaft. The surgical tool can include multiple flexible members configured to flex, either individually or as a group to cause movement of the end effector relative to the shaft. The movement of the end effector can include movement between an unarticulated, zero-angle position, in which the end effector is substantially longitudinally aligned with the shaft, and an articulated position, in which the end effector is angularly orientated relative to the shaft. The surgical tool can also include one or more homing members which are preferably rigid and are configured to be selectively actuated to force the end effector into the unarticulated, zero-angle position. The articulation of the end effector can thus be more precisely controlled since the end effector can be more accurately articulated from the unarticulated, zero-angle position. In other words, when one or more of the flexible members are actuated to cause the end effector to articulate (e.g., pitch, yaw, or combination thereof), an amount of the movement can be more accurately known to effect the desired direction and degree of articulation. The end effector may thus be more precisely positioned within a body of a patient in a surgical procedure and accordingly allow for more efficient performance of the surgical procedure and/or may reduce chances of the end effector moving to an unintended location and consequently damaging tissue and/or other matter.

Over time as the surgical tool is used in each of a plurality of surgical procedures on different patients, the multiple flexible members may change from their initial state (e.g., their state at a time of manufacturing or at first use of the surgical tool in a surgical procedure) due to the repeated use thereof. The change can include, for example, any one or more of a change in length (e.g., an increase in length due to being stretched out and/or twisted during use), a change in spring rate (e.g., a decrease in spring rate due to being stretched out and/or twisted during use), and a change in flexibility (e.g., an increase in flexibility due to being stretched out and/or twisted during use). The change results in less precisely controlled articulation of the end effector over time. The one or more homing members being able to force the end effector into the unarticulated, zero-angle position, which is a known position, will allow the degree of articulation of the end effector to be more precisely controlled.

FIG. 1 illustrates one embodiment of a surgical tool 10 that includes an elongate shaft (also referred to herein as a "shaft" and a "tool shaft") 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. The housing 18 includes various components configured to control the operation various features associated with the end effector 14 (e.g., any one or more of clamping, firing, rotation, articulation, energy delivery, etc.). In at least some embodiments, the shaft. 12, and hence the end effector 14 coupled thereto, is configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 can have other configurations, e.g., scissors, a babcock, a retractor, etc.

Figure 1A:
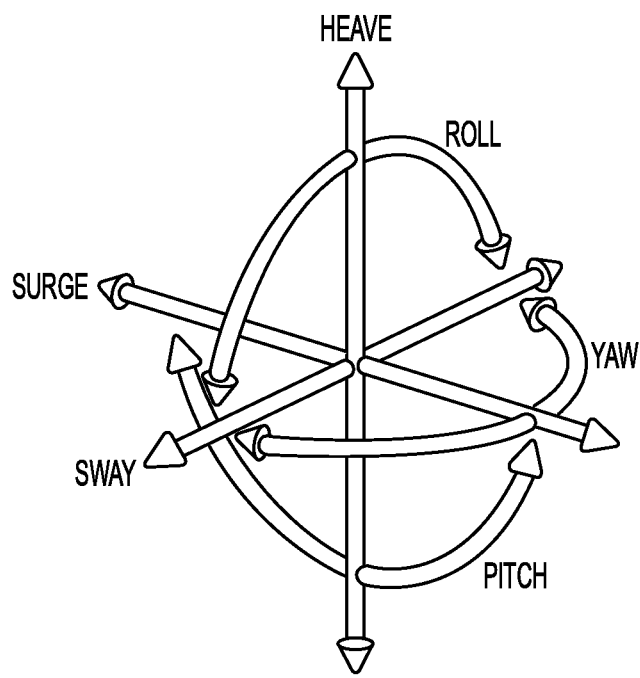
FIG. 1A is a graphical representation of terminology associated with six degrees of freedom.

The wrist 16 can have any of a variety of configurations. Exemplary embodiments of a wrist of a surgical tool are described in International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane. FIG. 1A illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 1A, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The surgical tool 10 includes a plurality of flexible members (obscured in FIG. 1) configured to effect the movement of the end effector 14 relative to the shaft 12. The flexible members are operably coupled to the tool housing 18, extend along the shaft 12, extend through the wrist 16, and are operably coupled to the end effector 14. In an exemplary embodiment, the flexible members extend distally from the tool housing 18 along the shaft 12 within an inner lumen of the shaft 12. The flexible members can be selectively actuated to cause the end effector 14 to pivot at the wrist 16 relative to the shaft 12. The selective actuation of the flexible members can cause any one or more of the flexible members to move, e.g., translate longitudinally, to cause the articulation. The one or more of the flexible members that translate depend on the requested articulation, e.g., the appropriate one or more of the flexible members flex to cause the end effector 14 to yaw and/or pitch as requested. The actuation can be accomplished in any of a variety of ways, such as by actuating an actuator operably coupled to the tool housing 18, as discussed further below. In general, the actuation applies tension to the one or more of the flexible members in a proximal direction to cause the one or more of the flexible members to translate and thereby cause the end effector 14 to articulate relative to the shaft 12. In other words, the actuation pulls the one or more of the flexible members proximally. The flexible members can also be selectively actuated to open and close the jaws 20, 22, e.g., to move the end effector 14 between open and closed positions. When both of the jaws 20, 22 are configured to move to open and close the end effector 14, at least one of the flexible members can be operably coupled to one of the jaws 20 to move that jaw 20 and at least one other of the flexible members can be operably coupled to the other one of the jaws 22 to move that jaw 22. When only one of the jaws 20, 22 is configured to move to open and close the end effector 14, at least one of the flexible members can be operably coupled to that one of the jaws 20, 22 to move that one of the jaws 20, 22.

The plurality of flexible members can have any of a variety of configurations, for example cables, rods, wires, or twisted strings. The flexible members can be made from any of a variety of materials, such as a metal (e.g., Tungsten, stainless steel, etc.). Exemplary embodiments of flexible members of a surgical tool are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

The movement of the end effector 14 caused by movement of one or more of the flexible members includes movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be aligned with the shaft 12 (e.g., be at a substantially zero angle) due to any number of factors, such as manufacturing tolerance and precision of measurement devices. The end effector 14 is shown in the unarticulated position in FIG. 1.

The surgical tool 10 includes one or more homing members (obscured in FIG. 1) that are configured to force the end effector 14 into the unarticulated, zero-angle position. The one or more homing members are operably coupled between the end effector 14 and the tool housing 18 and extend along the shaft 12. In an exemplary embodiment, the one or more homing members extend distally from the tool housing 18 along the shaft 12 within the inner lumen of the shaft 12. The one or more homing members can be configured to be selectively actuated to force the end effector 14 into substantial longitudinal alignment with the shaft 12. The selective actuation of the one or more homing members can cause all of the one or more of the homing members to engage the end effector 14 to force the end effector 14 into the substantially longitudinally aligned orientation. The actuation can be accomplished in any of a variety of ways, such as by actuating a second actuator operably coupled to the tool housing 18. In general, the actuation causes the one or more homing members to move in a distal direction relative to the shaft 12 to engage the end effector 14, and a subsequent actuation causes the one or more homing members to move in a proximal direction and disengage from the end effector 14.

In an exemplary embodiment, the one or more homing members are configured to move between a first position, in which the one or more homing members are not engaged with the end effector 14 and the end effector 14 is free to move between the unarticulated and articulated positions, and a second position, in which the one or more homing members are rigidly engaged with the end effector 14 and the end effector 14 is prevented from moving between the unarticulated and articulated positions (e.g., prevented from moving from the unarticulated position in which the end effector 14 is being held). In the first position, the one or more homing members are located proximal to the end effector 14 and proximal to the wrist 16 to help prevent the one or more homing members from interfering with the movement of the end effector 14 about the wrist 16. In at least some embodiments, the one or more homing members in the first position are entirely proximal to the end effector 14 and to the wrist 16 and are fully contained within the shaft 12. In the second position, at least distal ends of the one or more homing members are located distal to the shaft 12, distal to a proximal end of the end effector 14, and distal to the wrist 16 to help prevent the end effector 14 from moving about the wrist 16.

The one or more homing members can have any of a variety of configurations, for example an elongate rigid shaft/rod or an elongate rigid tube. Embodiments of homing members are further discussed below.

The one or more homing members can be configured to selectively engage the end effector 14 in any of a variety of ways. In an exemplary embodiment, the end effector 14 has one or more receiving elements each configured to receive therein one of the one or more homing members. The end effector 14 thus has a number of receiving elements equal to a number of the homing members. The one or more homing members in the first position are not received in the one or more receiving members so as to not be engaged with the end effector 14, and the one or more homing members in the second position are received in the one or more receiving members so as to be engaged with the end effector 14.

Figure 4:
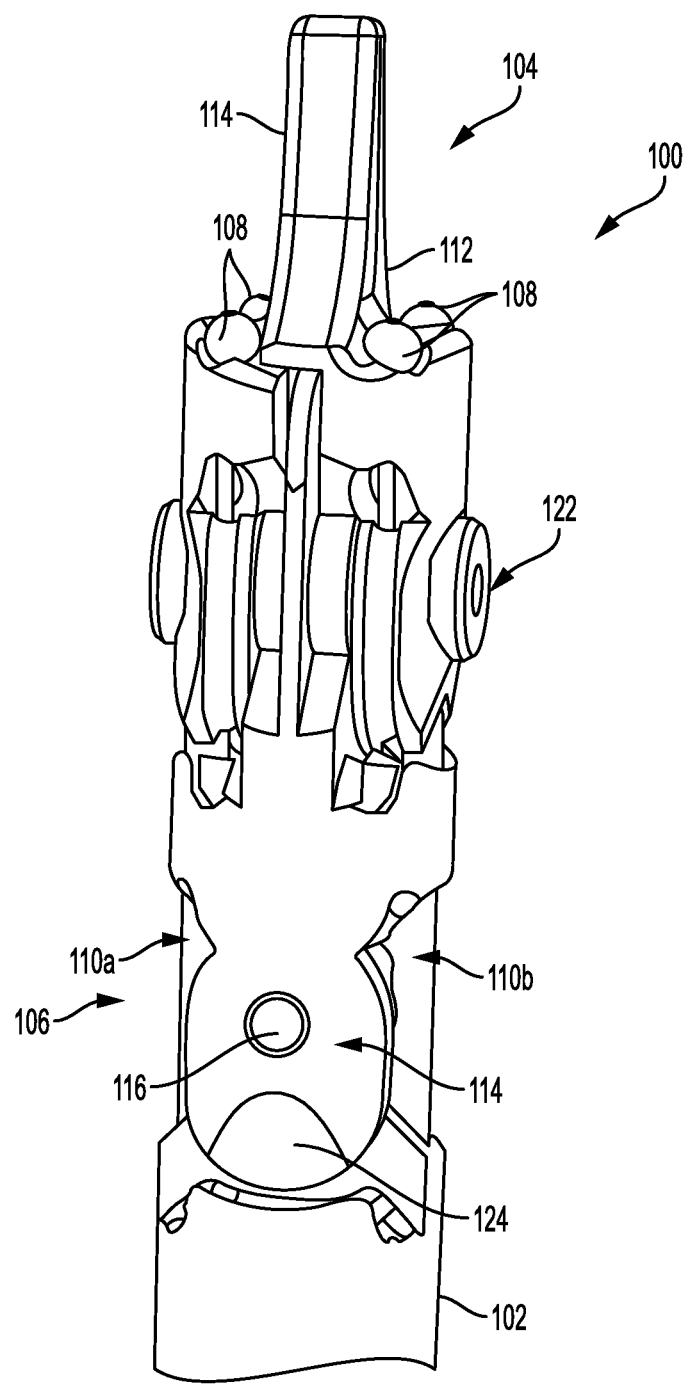
FIG. 4 is another perspective view of the distal portion of the surgical tool of FIG. 3.

The one or more receiving members can have any of a variety of configurations. For example, the one or more receiving members can include blind holes formed in the end effector 14 configured to receive therein a distal end of its associated one of the homing members. By way of example, receiving element 124 is shown in FIG. 4. In an embodiment including two homing members, each of the jaws 20, 22 can have one blind hole therein. The homing members being engaged with the end effector 14 can thus include each of the homing members engaging one of the jaws 20, 22. For another example, the one or more receiving members can include open channels (e.g., C-shaped grooves) formed in the end effector 14 configured to receive therein a distal end of its associated one of the homing members. In an embodiment including two homing members, each of the jaws 20, 22 can have one open channel therein. The homing members being engaged with the end effector 14 can thus include each of the homing members engaging one of the jaws 20, 22.

The tool housing 18 can have any of a variety of configurations. In general, the tool housing 18 can include one or more actuation mechanisms at least partially disposed therein configured to cause movement of the plurality of flexible members and thereby cause movement of the end effector 14 about the wrist 16. The one or more actuation mechanisms can include, for example, one or more movement mechanisms operably coupled to the plurality of flexible members, such as pulley(s) configured to be moved to cause translation of the flexible members. The tool housing 18 is configured to be releasably attached to a robotic surgical system (also referred to herein as a "robot" or "surgical robot") so as to releasably attach the tool 10 to the robot. The tool housing 18 can be configured to releasably attach to a robot in any of a variety of ways, as will be appreciated by a person skilled in the art, such as by clamping thereto, clipping thereto, or slidably mating therewith. The one or more movement mechanisms are configured to be controlled by the robot, as will be appreciated by a person skilled in the art, such as by the robot including one or more motors operably coupled to one or more inputs of the tool housing 18 that are operably coupled to the one or more movement mechanisms. The robot includes a computer system that can receive user inputs and can control the motor(s) in response to the user inputs and hence control movement of the flexible members and consequently the end effector 14. The one or more inputs of the tool housing 18 are also operably coupled to the one or more homing members to allow the robot to control movement of the one or more homing members.

Exemplary embodiments of robotic surgical systems are described in U.S. Pat. No. 8,831,782 entitled "Patient-Side Surgeon Interface For A Teleoperated Surgical Instrument" filed Jul. 15, 2013, which is hereby incorporated by reference in its entirety, and in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014. Also, exemplary embodiments of a tool housing of a surgical tool including one or more actuation mechanisms and configured to releasably attach to a robotic surgical system are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

In other embodiments, instead of being configured to releasably couple to a robotic surgical system, the tool housing 18 can be configured to be handheld by a user during use of the tool 10. The tool housing 18 in these embodiments can include a trigger, lever, or other actuator configured to be manually or electronically manipulated to cause movement of the flexible members, as will be appreciated by a person skilled in the art. The tool housing 18 in these embodiments can also include a trigger, lever, or other actuator configured to be manually manipulated to cause movement of the one or more homing members, as will also be appreciated by a person skilled in the art.

The surgical tool 10 can include a plurality of sensors (obscured in FIG. 1) configured to sense a position of each of the plurality of flexible members at least when the end effector 14 is in the unarticulated position. In an exemplary embodiment, a number of the sensors equals a number of the flexible members, with each one of the sensors being associated with and being configured to sense the position of an associated one of the flexible members. The sensors can be located in any of a variety of places on the tool 10. For example, the sensors can be disposed within the tool housing 18. The sensors being contained within the tool housing 18 may help protect the sensors from inadvertent damage and/or help prevent any outside pressures from affecting the readings of the sensors. For another example, the sensors can be attached to the end effector 14. For yet another example, the sensors can be attached to the wrist 16.

The sensors can have any of a variety of configurations. For example, any one or more of the sensors can include a torque (force) sensor, a position sensor, or a load cell.

The sensors are configured to be in electronic communication with at least one processor configured to process data received from the sensors. The at least one processor can be on board the tool 10, e.g., disposed within the tool housing 18 thereof, or can be located elsewhere, such as part of a robotic surgical system to which the tool 10 is releasably attached. The data received by the at least one processor from the sensors includes data that is indicative of the sensed position of each of the flexible members when the end effector 14 is in the unarticulated position, e.g., when the one or more homing members are forcing the end effector 14 into the unarticulated position. The at least one processor is configured to cause the received data that is indicative of the sensed position of each of the flexible members when the end effector 14 is in the unarticulated position to be a stored in a memory. The memory can be on board the tool 10, e.g., disposed within the tool housing 18 thereof, or can be located elsewhere, such as part of a robotic surgical system to which the tool 10 is releasably attached.

The at least one processor is configured to use the received and stored data that is indicative of the sensed position of each of the flexible members when the end effector 14 is in the unarticulated position as a home position of the flexible members. In response to the flexible members being actuated to move the end effector 14, the at least one processor can be configured to determine an amount of force to be applied to each of the flexible members in view of the home position to effect the requested movement of the end effector 14. In other words, by knowing an amount of force applied to each of the flexible members in the home position (in the case of force sensors) or a position of each of the flexible members in the home position (in the case of position sensors), the at least one processor can determine how much to tension each of the flexible members (e.g., how much to pull each of the flexible members) to accurately achieve the requested movement of the end effector 14. In this way, even if the flexible members have changed from the initial state over time, as discussed above, the home position will reflect their current state and allow the flexible members to be precisely controlled and hence the movement of the end effector 14 to be precisely controlled.

In an exemplary embodiment, before sensing the position of each of the flexible members when the end effector 14 is in the unarticulated position, a predetermined amount of tension in a proximal direction is applied to each of the flexible members, e.g., each of the flexible members is pulled with a predetermined amount of force. Tensioning each of the flexible members before sensing their tension with the sensors allows the position of the flexible members to be determined when the flexible members are experiencing a known amount of tension. The predetermined amount of tension can vary based on a variety of factors, such as a spring rate of the flexible members, a power output capacity of the motors used to effect the movement of the flexible members, etc. The predetermined amount of tension can be, for example, about 5 lb.

In at least some embodiments, the home position is automatically gathered in response to actuation of the one or more homing members. In this way, the home position may be gathered when the end effector 14 is known to be in the unarticulated position. In an exemplary embodiment, the home position is gathered at a start of a use of the surgical tool 10. For example, after coupling the tool 10 to a robotic surgical system, the home position can be gathered and thereby establish a baseline or initial position of the tool 10 so that when any of the flexible members are flexed to effect a desired movement of the tool 10, the flexible members are flexed with reference to the home position.

In at least some embodiments, the home position is automatically gathered in response to the wrist 16 being retracted into a trocar (or other access device) through which the tool 10 has been advanced into a body of a patient. This automatic gathering may help minimize the time delay associated with advancement and retraction of the one or more homing members. The end effector 14 will be in the unarticulated position to be retracted into the trocar, so the wrist 16 being retracted into the trocar will indicate that the end effector 14 is in the unarticulated position at which the home position can be accurately gathered. The wrist 16 being retracted into the trocar can be detected in any number of ways, such as by a scope or other visualization device inserted into the patient "seeing" that the wrist 16 has been so retracted, by the tool 10 including a motion sensor configured to sense translational movement of the shaft 12 indicative of the wrist 16 being retracted into the trocar (e.g., proximal translational movement of the shaft 12 equal to or within a predetermined threshold amount of an amount of distal translation movement of the shaft 12 to advance the shaft 12 into the body of the patient, etc.), etc.

In at least some embodiments, the home position is automatically gathered in response to the wrist 16 being advanced distally beyond a distal end of a trocar (or other access device) through which the tool 10 is being advanced into a body of a patient. This automatic gathering may help minimize the time delay associated with advancement and retraction of the one or more homing members. The end effector 14 will be in the unarticulated position to be advanced through the trocar, so the wrist 16 being advanced distally beyond the trocar's distal end will indicate that the end effector 14 is in the unarticulated position at which the home position can be accurately gathered. The wrist 16 being advanced distally beyond the trocar's distal end can be detected in any number of ways, such as by a scope or other visualization device inserted into the patient "seeing" that the wrist 16 has been so advanced, by the tool 10 including a motion sensor configured to sense translational movement of the shaft 12 indicative of the wrist 16 being fully advanced through the trocar (e.g., distal translational movement of the shaft 12 equal to or within a predetermined threshold amount of a known length of the trocar, etc.), etc.

Although the home position of the tool 10 is configured to be gathered when the end effector 14 is in the unarticulated position, in at least some embodiments, the home position can be configured to be additionally or alternatively gathered when the end effector 14 is in the articulated position at a predetermined angle relative to the shaft 12. For example, the home position can be configured to be additionally or alternatively gathered when the end effector 14 is at a maximum articulated angle relative to the shaft 12. The home position being able to be gathered when the end effector is articulated may provide more surgeon flexibility by allowing the home position to be gathered when the tool 10 is in use in a patient and has already had its end effector 14 articulated. The home position being gatherable when the end effector 14 is in the unarticulated position may allow the home position to be easily gathered at a start of a surgical procedure since the end effector 14 is typically unarticulated at the start of the procedure to facilitate insertion of the end effector 14 in a body of a patient.

Figures 2, 3:
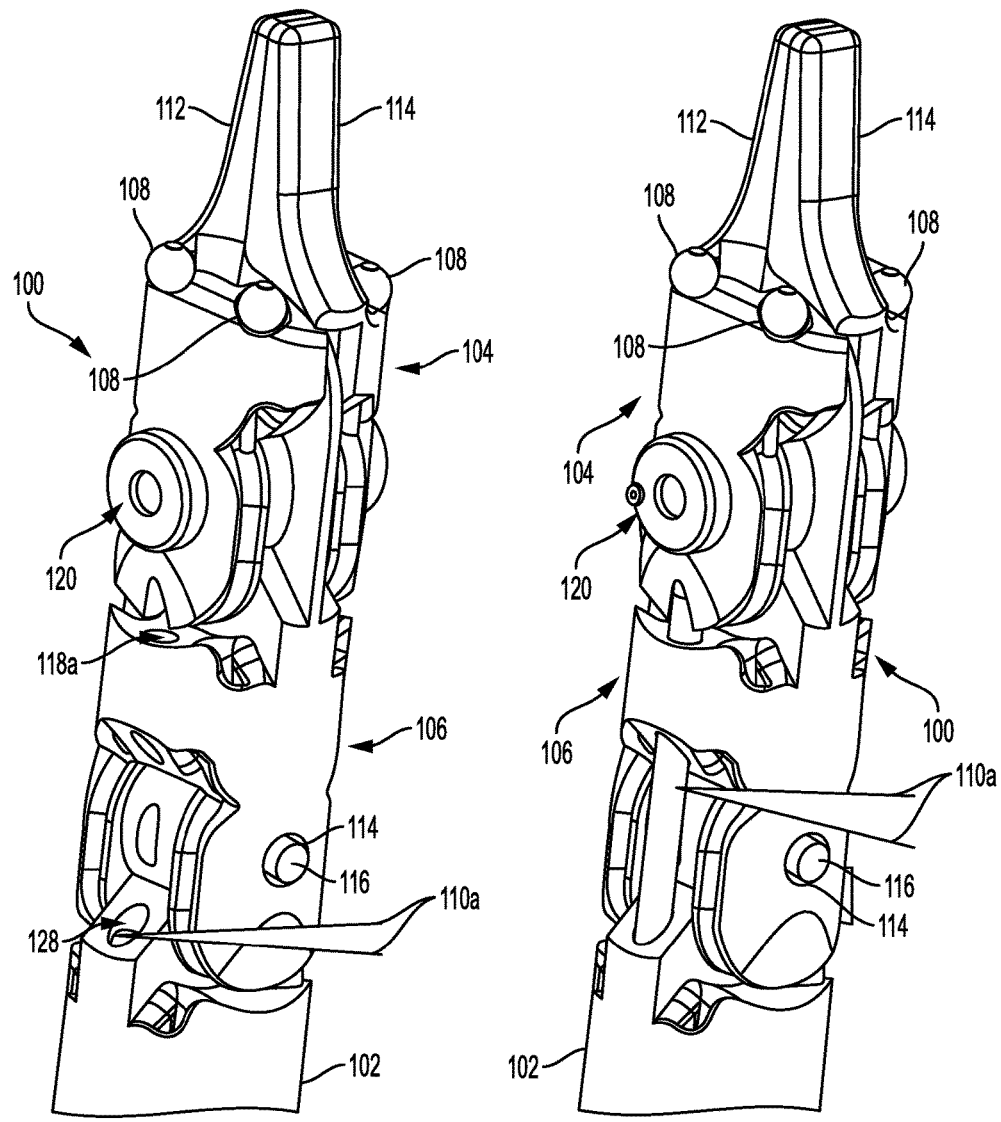
FIG. 2 is a perspective view of a distal portion of another embodiment of a surgical tool with homing members of the surgical tool in a retracted position.
FIG. 3 is a perspective view of the distal portion of the surgical tool of FIG. 2 with the homing members in an advanced position.

FIGS. 2-8 illustrate an exemplary embodiment of a surgical tool 100 that includes an elongate shaft 102, an end effector 104 including a pair of opposed jaws 112, 114, a wrist 106 that couples the end effector 104 to the shaft 102 at a distal end of the shaft 102, a tool housing (not shown) coupled to a proximal end of the shaft 102, a plurality of flexible members 108, and one or more homing members 110*a*, 110*b* in the form of rigid members. The tool 100 is configured and used similar to the tool 10 of FIG. 1. Only a distal portion of the tool 100 is shown in FIGS. 2-8. FIGS. 2-8 show the end effector 104 in an unarticulated position. FIG. 2 shows the one or more homing members 110*a*, 110*b* in a first position, in which the one or more homing members 110*a*, 110*b* are not engaged with the end effector 104 and the end effector 104 is free to move between its unarticulated and articulated positions. FIGS. 3-8 show the one or more homing members 110*a*, 110*b* in a second position, in which the one or more homing members 110*a*, 110*b* are engaged with the end effector 104 and the end effector 104 is prevented by the one or more homing members 110*a*, 110*b* from moving between the unarticulated and articulated positions. FIGS. 2-8 show the end effector 104 in a closed position.

Figure 5:
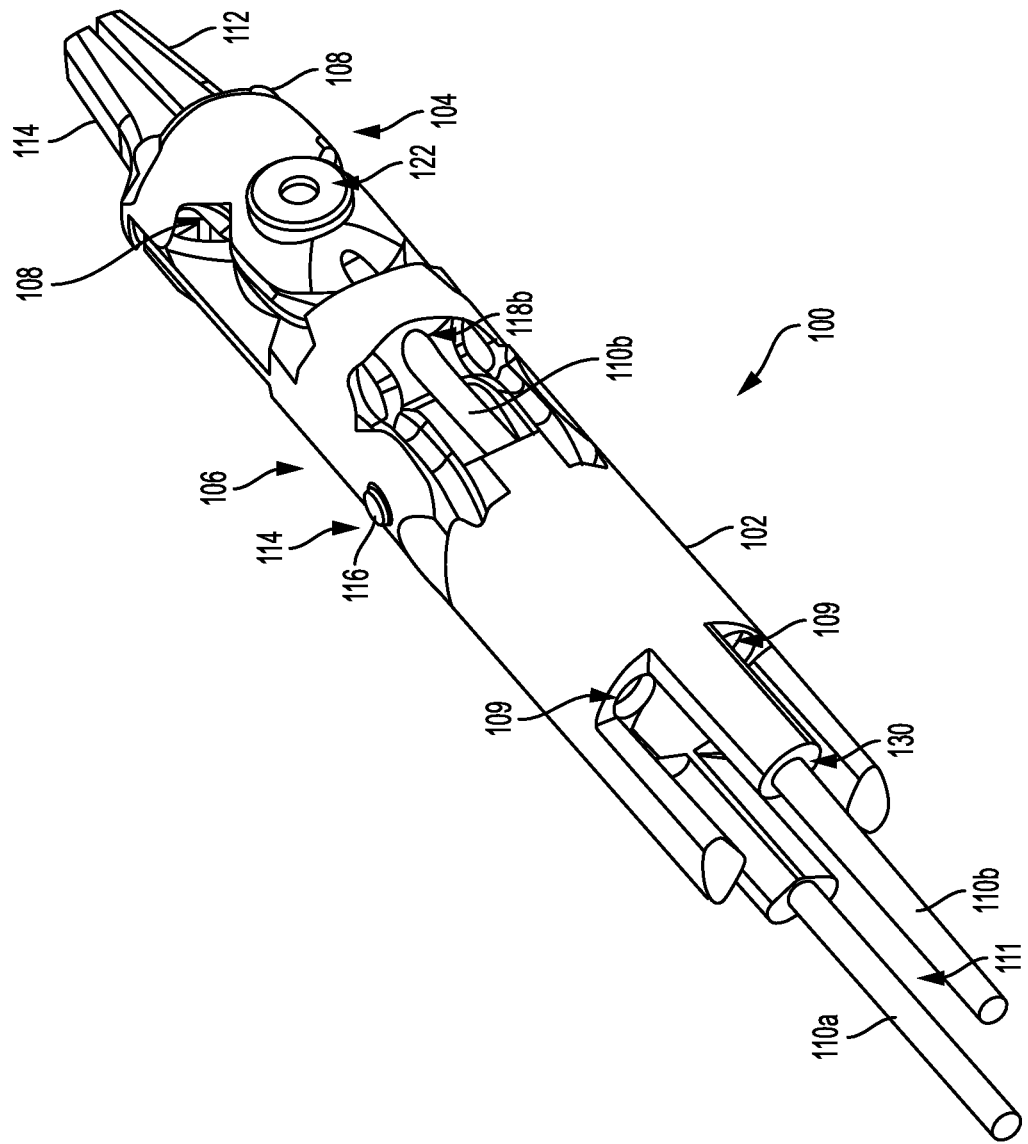
FIG. 5 is yet another perspective view of the distal portion of the surgical tool of FIG. 3.
Figure 6:
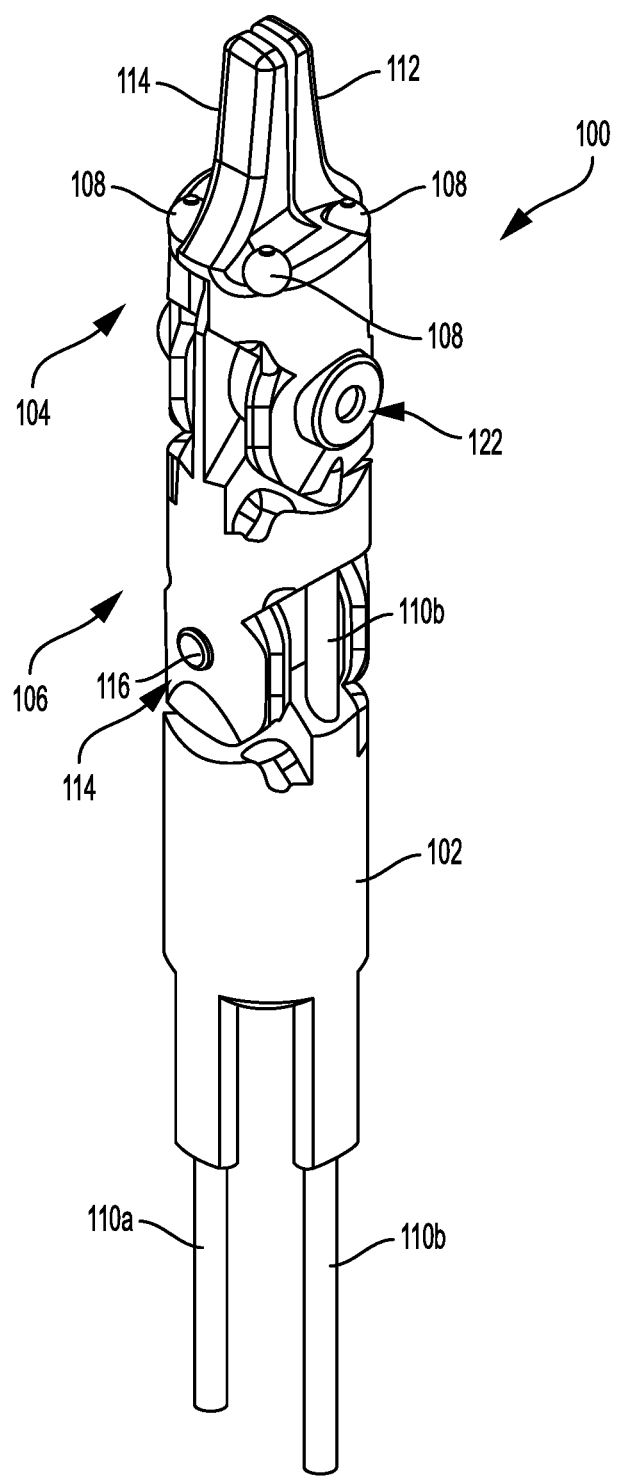
FIG. 6 is still another perspective view of the distal portion of the surgical tool of FIG. 3.
Figures 7, 8:
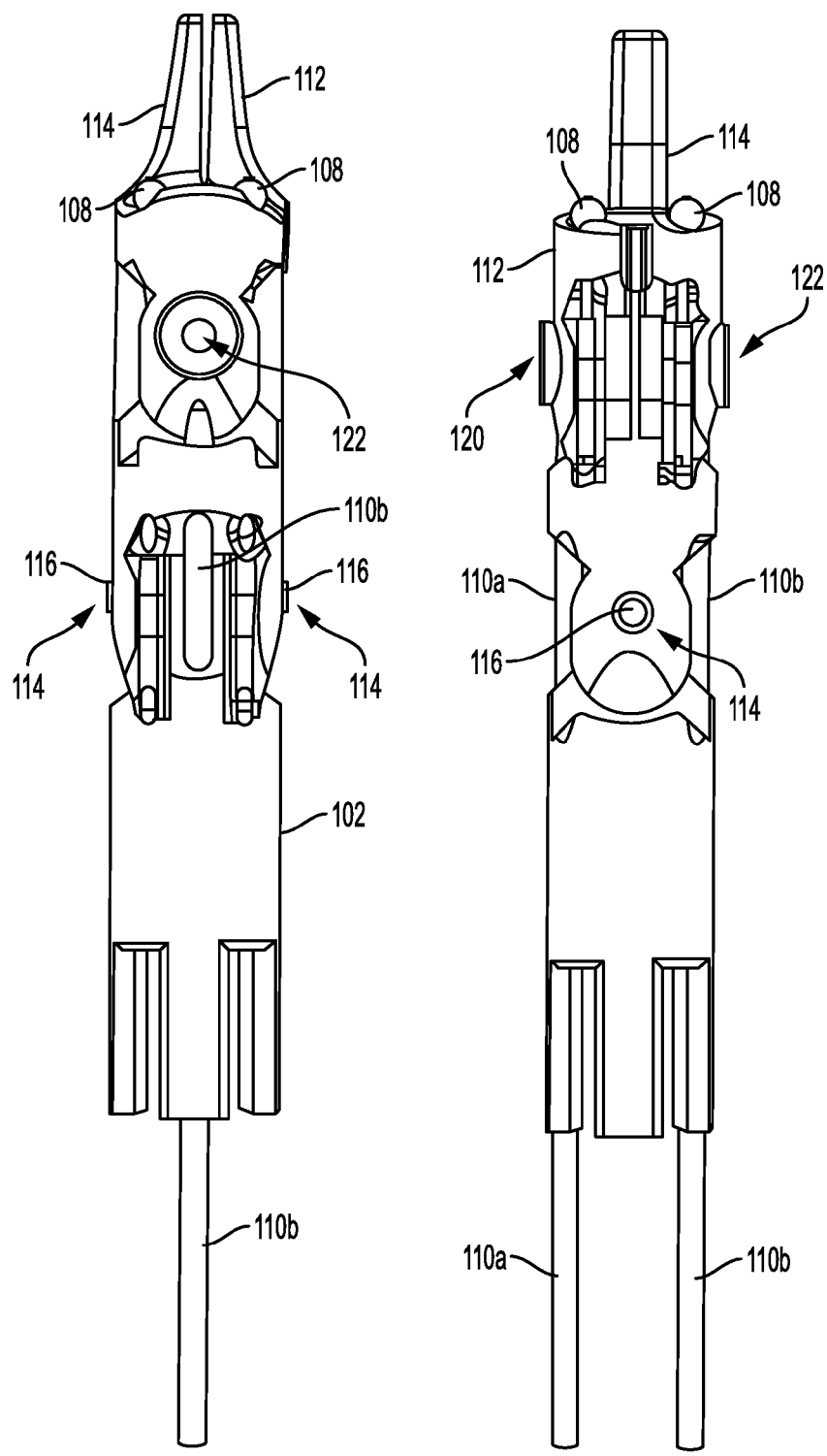
FIG. 7 is a side view of the distal portion of the surgical tool of FIG. 3.
FIG. 8 is another side view of the distal portion of the surgical tool of FIG. 3.
Figure 9:
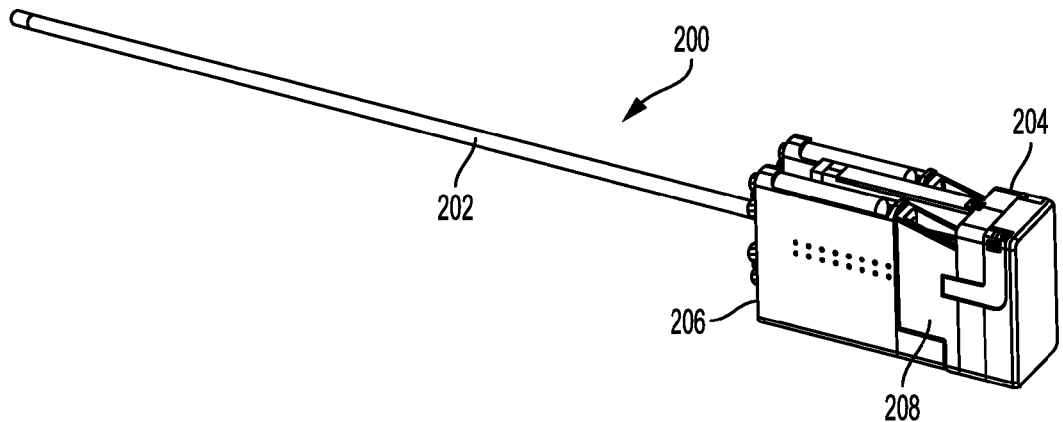
FIG. 9 is a perspective of a portion of another embodiment of a surgical tool coupled to one embodiment of a tool driver and sterile barrier of a robotic surgical system.
Figure 10:
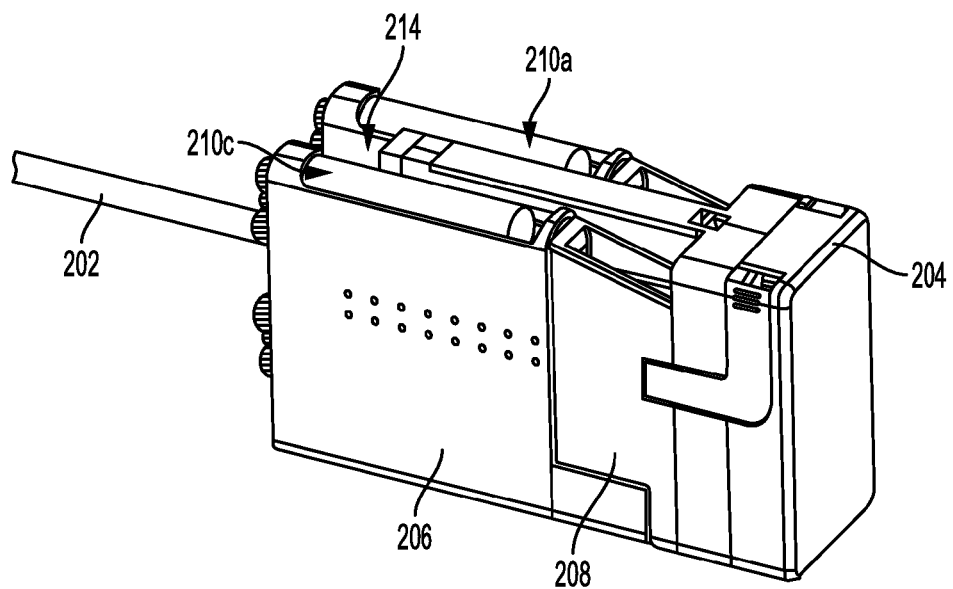
FIG. 10 is a perspective view of the tool driver, sterile barrier, and a proximal portion of the surgical tool of FIG. 9.
Figure 11:
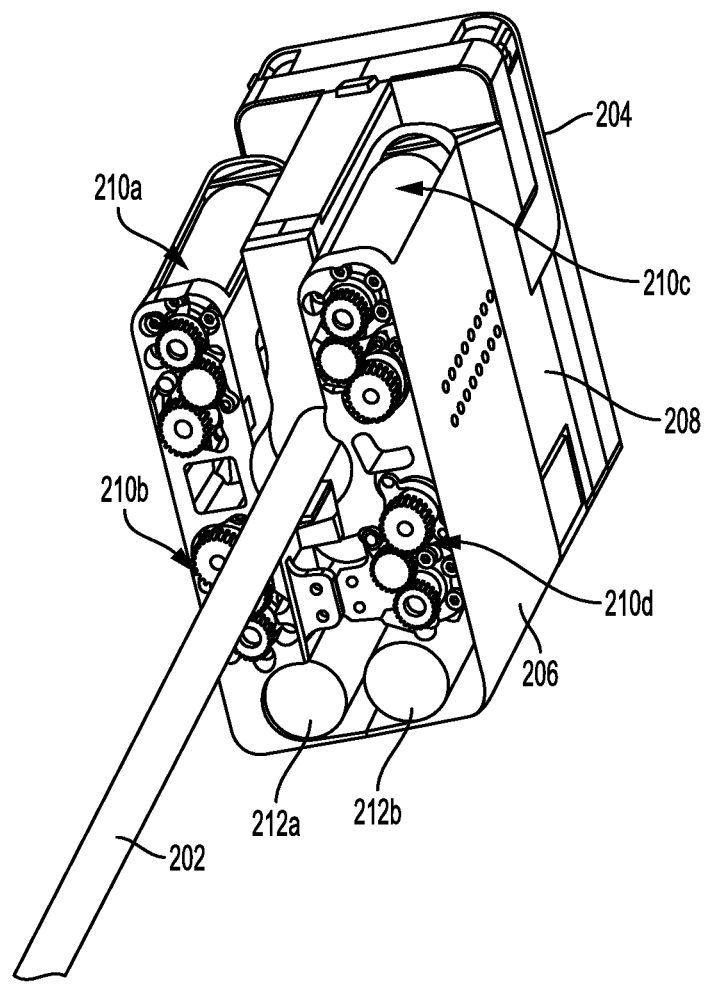
FIG. 11 is another perspective view of the tool driver, sterile barrier, and the proximal portion of the surgical tool of FIG. 10.

The tool 100 includes four flexible members 108, but any number of flexible members can be used. Only a distal portion of the flexible members 108 are shown in FIGS. 2-8 for clarity of illustration. The flexible members 108 extend proximally from the end effector 104 to the tool housing, as discussed herein. As best shown in FIG. 5, the shaft 12 includes a plurality of lumens or bores 109 formed therein configured to receive the flexible members 108 therethrough. Two of the bores 109 are visible in FIG. 5, with the other two bores 109 being obscured. As shown, the bores 109 are spaced radially around an inner lumen 111 of the shaft 102.

The one or more homing members 110*a*, 110*b* include two homing members 110*a*, 110*b* in this illustrated embodiment, one associated with each one of the jaws 112, 114. The one or more homing members 110*a*, 110*b* are in the form of elongate rigid rods in this illustrated embodiment. As discussed further below, the shaft 102 includes bores 128, 130 on opposed sides thereof positioned radially around the shaft's inner lumen and offset from the flexible members.

The tool 100 includes a first joint 114 at which the wrist 106 is pivotally coupled to the shaft 102. In particular, a proximal end of the wrist 106 is coupled to a distal end of the shaft 102 at the first joint 114. The shaft 102 and the wrist 106 each have holes formed therein in which a first pin 116 is positioned at the first joint 114. The first pin 116 includes two pins in this illustrated embodiment on either opposed side of the first joint 114, but the first pin 116 can be a single pin. The wrist 106 is configured to rotate at the first joint 114 about the first pin 116 relative to the shaft 102 to cause movement of the end effector 104, in particular movement that causes articulation of the end effector 104 relative to the shaft 102. Actuation of the flexible members 108 is configured to cause the movement of the wrist 106 at the first joint 114, and hence to cause articulation of the end effector 104, as discussed herein. The wrist 106 in this illustrated embodiment is configured to pivot about the first joint 114 in a single plane, e.g., in one of pitch and yaw.

The one or more homing members 110*a*, 110*b* in the second position extend through one or more bores 118*a*, 118*b* formed in the wrist 106. The one or more homing members 110*a*, 110*b* in the second position thus prevent the wrist 106 from pivoting at the first joint 114. The one or more homing members 110*a*, 110*b* in the first position do not extend through the one or more bores 118*a*, 118*b* and therefore do not prevent the wrist 106 from pivoting at the first joint 114.

The tool 100 includes second and third joints 120, 122 configured to facilitate movement of the end effector 104 between its closed and open positions. The second and third joints 120, 122 can share a common axis, and this can be considered to be a single joint. The first jaw 112 is configured to pivot about the second joint 120, and the second jaw 114 is configured to pivot about the third joint 122. Actuation of the flexible members 108 is configured to cause the movement of the first jaw 112 at the second joint 120 and of the second jaw 114 at the third joint 122. In an exemplary embodiment, the jaws 112, 114 are configured to pivot in tandem at their respective joints 120, 122. In other words, during opening of the jaws 112, 114 each of the jaws 112, 114 rotates at its associated joint 120, 122, and during closing of the jaws 112, 114 each of the jaws 112, 114 rotates at its associated joint 120, 122.

The one or more homing members 110a, 110b in the second position are received in respective receiving elements of the first and second jaws 112, 114. The one or more homing members 110a, 110b in the second position thus prevent the jaws 112, 114 from opening and closing. The one or more homing members 110a, 110b in the first position are not seated in the receiving elements and thus do not restrict opening and closing of the jaws 120, 122. The one or more homing members 110a, 110b are thus configured to prevent movement of the end effector 114 at all three of the joints 114, 120, 122 when the one or more homing members 110a, 110b are in the second position.

The receiving elements are in the form of recesses or open channels formed in a distal surface of the end effector 104, e.g., in distal surfaces of the jaws 112, 114. The receiving elements are configured to longitudinally align with the one or more bores 118a, 118b formed in the wrist 106. In this way, the one or more homing members 110a, 110b can extend through the one or more bores 118a, 118b and have their distal ends seated in the receiving elements. The open channels each have a tapered shape that tapers in a distal direction such that the channels are wider at their proximal ends than at their distal ends. The wider proximal ends of the channels may help the one or more homing members 110a, 110b force the end effector 104 into its unarticulated position, if it is not already in the unarticulated position when the one or more homing members 110a, 110b are actuated, by helping to guide the distal ends of the one or more homing members 110a, 110b into their respective receiving elements. The distal ends of the one or more homing members 110a, 110b are tapered in a distal direction, which may also help guide them into their respective receiving elements.

The shaft 102 has one or more bores 128, 130 formed therein configured to slidably seat the one or more homing members 110a, 110b therein. The shaft's one or more bores 128, 130 are configured to longitudinally align with the wrist's one or more bores 118a, 118b. The receiving elements are thus configured to longitudinally align with the shaft's one or more bores 128, 130. In this way, the one or more homing members 110a, 110b can extend through the shaft's one or more bores 128, 130 and through the wrist's one or more bores 118a, 118b and have their distal ends seated in the receiving elements. When the one or more homing members 110a, 110b are in the first position, as shown in FIG. 2, the one or more homing members 110a, 110b do not extend distally beyond the shaft's one or more bores 128, 130. The one or more homing members 128, 130 may thus be "hidden" and be less likely to interfere with any operation of the tool 100.

In another embodiment of a surgical tool, the tool can be configured and used similar to the tool 100 of FIGS. 2-8 but instead of including two homing members, the tool 100 can include a single homing member. The single homing member can be radially offset from the elongate shaft's longitudinal axis. Each of the homing members 110a, 110b are radially offset from the shaft's longitudinal axis in the embodiment of FIGS. 2-8, and in this alternate embodiment, the tool can include only one of these radially offset homing members. The tool's wrist can have one bore configured to slidably receive the homing member therethrough, and the tool's end effector can have one receiving element configured to receive the one homing member therein. The end effector, if it includes a pair of opposed jaws, can have the one receiving element formed in one of the jaws. When the homing member is actuated to force the end effector into its unarticulated position, the one homing member would only force one of the jaws to its closed position. The other one of the jaws can be closed against the forced one of the jaws, such as by actuating the closure mechanism of the tool (e.g., actuating one or more flexible members of the tool to close the jaw).

In another embodiment of a surgical tool including a single homing member, the tool can be configured and used similar to the tool 100 of FIGS. 2-8 but the single homing member can be substantially longitudinally aligned with the elongate shaft's longitudinal axis. The tool's wrist can have one bore configured to slidably receive the homing member therethrough, and the tool's end effector can have one receiving element configured to receive the one homing member therein.

In another embodiment of a surgical tool including a single homing member, the tool can be configured and used similar to the tool 100 of FIGS. 2-8 but the one or more homing members can be in the form of an elongate tube. The elongate tube can be configured to selectively move over at least a proximal portion of the tool's wrist and over at least a proximal portion the tool's end effector to force the end effector to its unarticulated position. The elongate tube in its second position in which it forces the end effector to the unarticulated position can be positioned over a first joint of the tool about which the wrist can pivot to articulate the end effector and can be positioned over second and third joints of the tool about which jaws of the end effector can pivot to open and close the end effector. In this way, the elongate tube can prevent movement of the end effector, both opening/closing and articulating. The tool's elongate shaft can contain the tube therein when the tube is in its first position in which it does not constrain movement of the end effector.

In another embodiment of a surgical tool, the tool can be configured and used similar to the tool 100 of FIGS. 2-8 but instead of the one or more homing members being movable via the tool's flexible members, the one or more homing members can be configured to be moved via a rotary coupling, as discussed further below.

FIGS. 9-15 illustrate another embodiment of a surgical tool 200 that includes an elongate shaft 202, an end effector (not shown), a wrist (not shown) that couples the end effector to the shaft 202 at a distal end of the shaft 202, a tool housing 204 coupled to a proximal end of the shaft 202, a plurality of flexible members (not shown), and one or more homing members (not shown). The tool 200 is configured and used similar to the tool 10 of FIG. 1. Only a proximal portion of the tool 200 is shown in FIGS. 9-15. This proximal portion of the tool 200 can be the proximal portion of the tool 10 of FIG. 1 or the proximal portion of the tool 100 of FIGS. 2-8. An outer casing of the tool housing 204 is removed for illustrative purposes from FIGS. 13 and 14.

Figure 12:
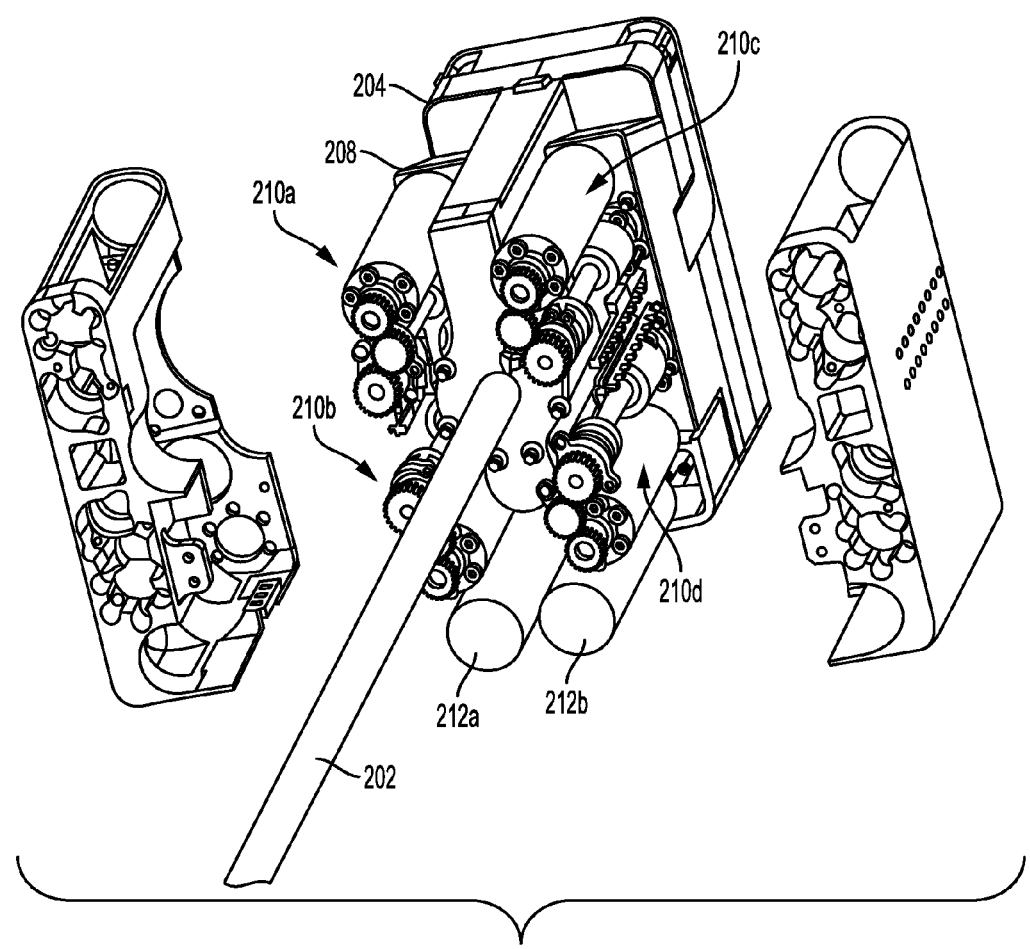
FIG. 12 is a perspective, partially exploded view of the tool driver, sterile barrier, and the proximal portion of the surgical tool of FIG. 10.
Figure 13:
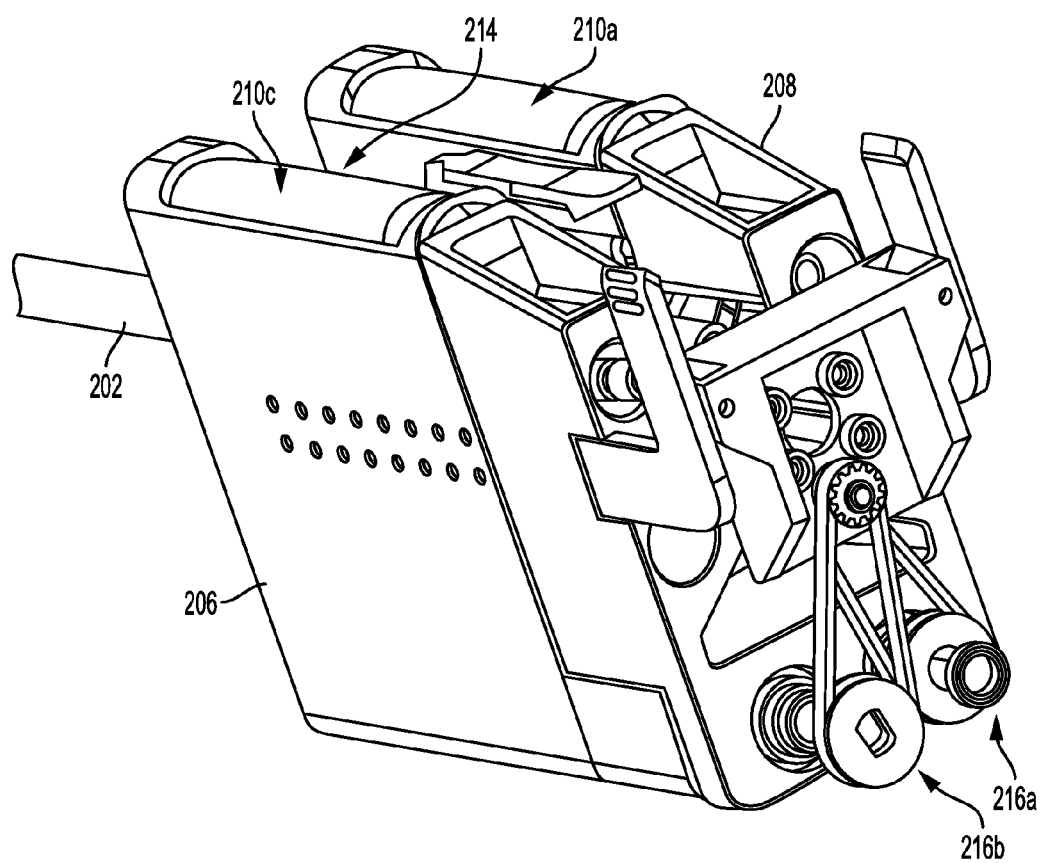
FIG. 13 is a perspective view of the tool driver, sterile barrier, and the proximal portion of the surgical tool of FIG. 10 with an outer casing of a housing of the surgical tool removed for illustrative purposes.
Figure 14:
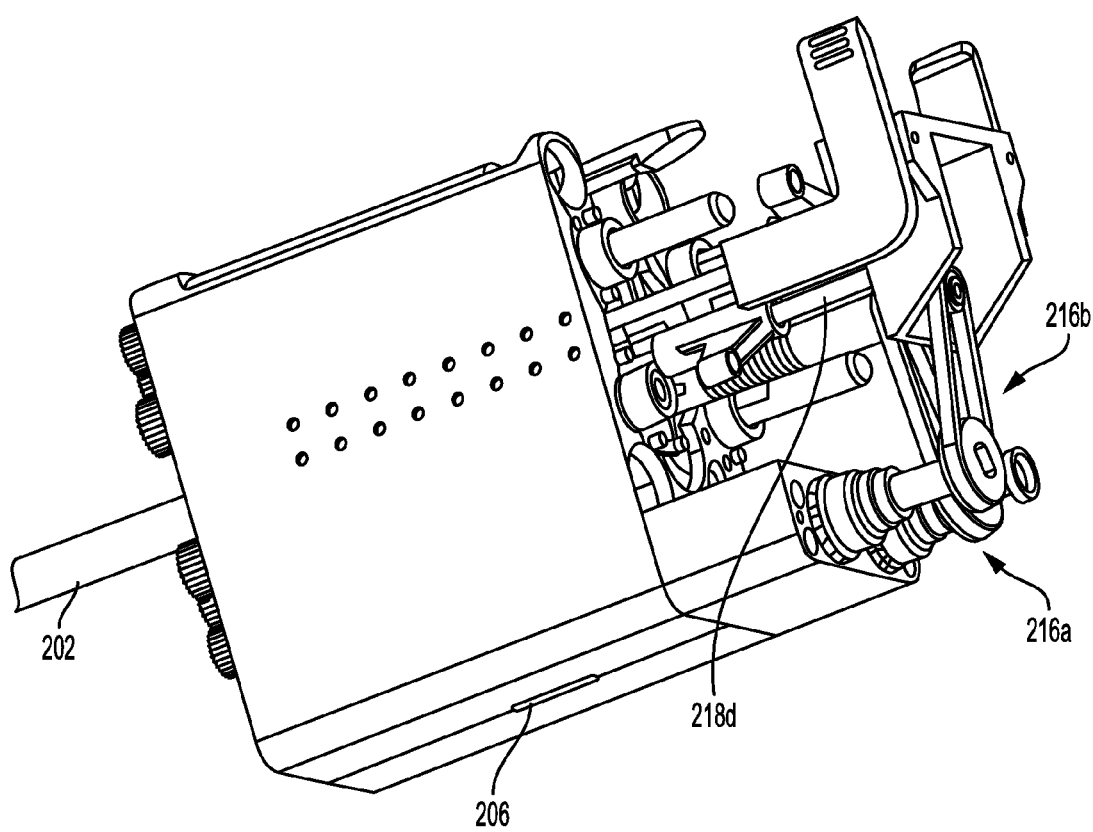
FIG. 14 is another perspective view of the tool driver, sterile barrier, and the proximal portion of the surgical tool of FIG. 13.
Figure 15:
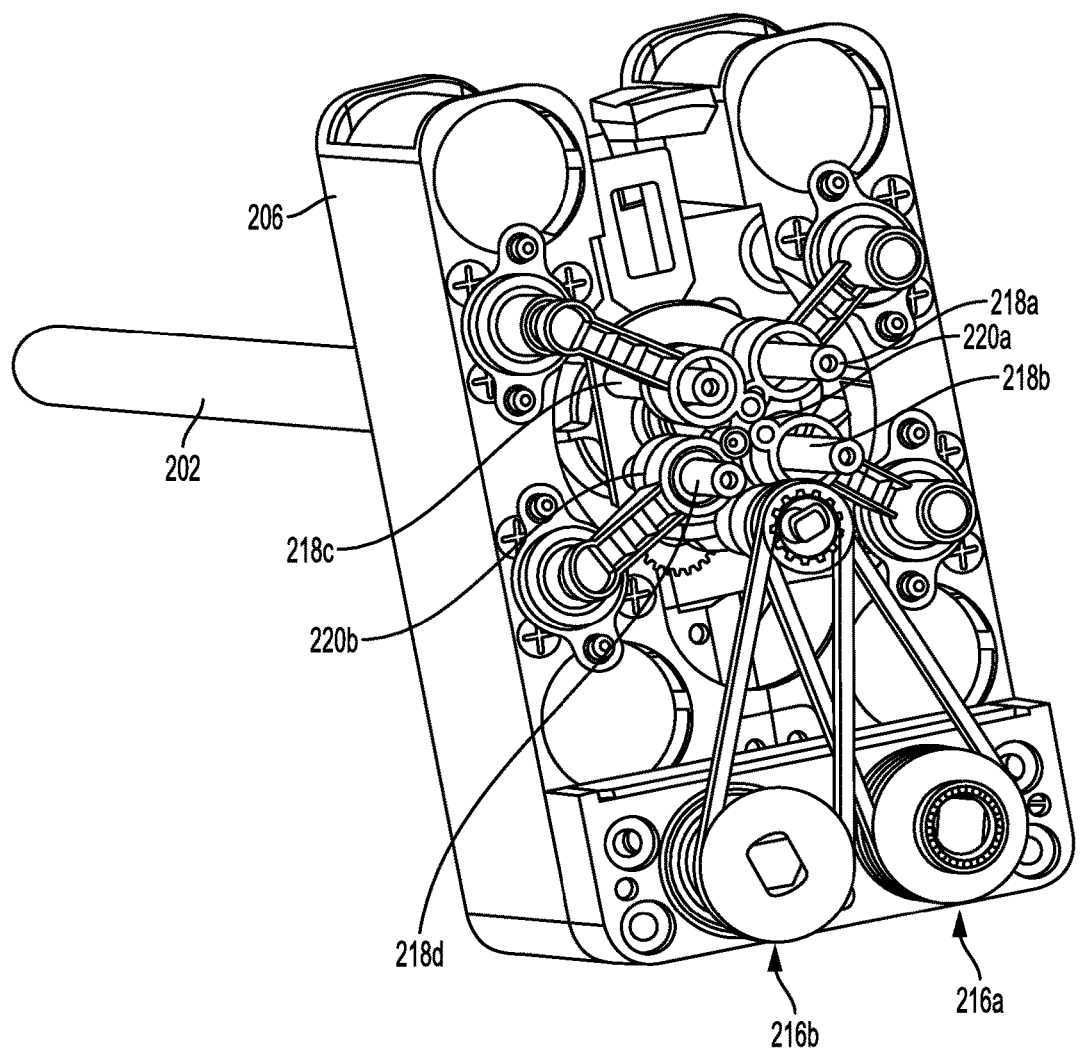
FIG. 15 is a perspective view of the tool driver and a proximal portion of the surgical tool of FIG. 9 with the outer casing of a housing of the surgical tool removed for illustrative purposes.

FIGS. 9-15 show the tool 200 releasably coupled to one embodiment of a robotic surgical system. The tool housing 204 is releasably coupled to a tool driver 206 of the robotic surgical system with the shaft 202 of the tool 200 extending distally from the tool housing 204 and the tool driver 206. Only a partial portion of the robotic surgical system is shown in FIGS. 9-15 for clarity of illustration. FIG. 12 shows an outer casing of the tool driver 206 in exploded view for illustrative purposes.

The robotic surgical system also includes a sterile barrier 208 to which a sterile shroud or drape (not shown) can be attached for sterility purposes, as will be appreciated by a person skilled in the art. The placement of the sterile barrier 208 between the tool housing 204 and the tool driver 206 may ensure a sterile coupling point for the tool 200 and the robot and thereby permit removal the tool 200 from the robot to exchange with other surgical tools during the course of a surgery without compromising the sterile surgical field.

The tool driver 206 can have any of a variety of configurations, as will be appreciated by a person skilled in the art. The tool driver 206 includes one or more motors for controlling a variety of movements and actions associated with tools such as the tool 200 that can be releasably coupled to the tool driver 206, as will be appreciated by a person skilled in the art. In this illustrated embodiment, the tool driver 206 includes six motors, four motors 210a, 210b, 210c, 210d for driving movement/action using activation features and one motor 212a, 212b for each of two rotary couplings of the tool driver 206 for driving movement/action through rotary motion. For example, each motor 210a, 210b, 210c, 210d, 212a, 212b can couple to and/or interact with an activation feature (e.g., gear) associated with the tool 200 for controlling one or more actions and movements that can be performed by the tool 200, such as movement of the tool's flexible members relative to the shaft 202, movement of the tool's one or more homing members relative to the shaft 202, articulation of the tool's end effector, rotation of the shaft 202 about its longitudinal axis, etc. The motors 210a, 210b, 210c, 210d, 212a, 212b are accessible through a proximal end of the sterile barrier 208, and the tool housing 204 of the tool 200 is configured to mount on the proximal end of the sterile barrier 208 to couple to the sterile barrier 208 and the tool driver 206. Exemplary embodiments of motors and movements and actions motors can drive are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

Each of the four motors 210a, 210b, 210c, 210d is operably coupled to one of the tool's flexible members via a coupling member 218a, 218b, 218c, 218d disposed within the tool housing 204. The movement of the flexible members (e.g., pulling thereof in a proximal direction) can thus be independently controlled by their associated one of the motors 210a, 210b, 210c, 210d. Rotary motion of the motors 210a, 210b, 210c, 210d can thus be configured to cause translational movement of the flexible members.

One of the rotary couplings is driven by one of the motor 212a to rotate the shaft 202. The tool housing 206 includes a first pulley system 216a operably coupled to the first rotary coupling to transfer the power of the motor 212a to the shaft 202 for rotation thereof. Rotary motion can thus be configured to cause rotational movement, of the shaft 202.

Another one of the rotary couplings is driven by another one of the motors 212b to cause the translational movement of the one or more homing members (e.g., distal movement to advance the one or more homing members to force the end effector to its unarticulated position and proximal movement to retract the one or more homing members). The tool housing 206 includes a second pulley system 216b operably coupled to the second rotary coupling to transfer the power of the motor 212b to the one or more homing members for longitudinal translation thereof via a lead screw (also referred to herein as a "drive screw"). Rotary motion can thus be configured to cause translational movement of the one or more homing members.

In another embodiment, a number of the motors 210a, 210b, 210c, 210d equal to a number of the one or more homing members are operably coupled to the tool's one or more homing members via coupling members 220a, 220b disposed within the tool housing 204. Two coupling members 220a, 220b are shown, corresponding to two homing members. The motors 210b, 210d can operate in tandem to cause movement of the one or more homing members (e.g., distal movement to advance the one or more homing members to force the end effector to its unarticulated position and proximal movement to retract the one or more homing members). The motors 210b, 210d can thus be configured to cause translational movement of the one or more homing members.

The tool driver 206 includes a receiving channel 214 formed in a wall thereof (a top wall in this illustrated embodiment) for receiving a distal portion of the tool housing 204 and a proximal portion of the shaft 202 of the tool 200. In other embodiments, the tool housing 204 and shaft 202 can extend through an opening formed in the tool driver 206, or the tool 200 and the tool driver 206 can mate in various other ways. The sterile barrier 208 also includes a receiving channel 216 formed in a wall thereof (a top wall in this illustrated embodiment) for receiving a distal portion of the tool housing 204 but can also mate thereto in various other ways. A proximal end of the shaft 202 is located distal to the sterile barrier 208. In other words, the shaft 202 does not extend proximally far enough to reach the sterile barrier 208. The shaft 202 can thus be contained within the sterile surgical area.

The tool housing 204 includes features configured to assist with releasably coupling the tool housing 204 to the tool driver 206, and hence for coupling the tool 200 to the robotic surgical system. The tool housing 204 includes gears and/or actuators configured to be actuated by one or more of the motors 210a, 210b, 210c, 210d, 212a, 212b. The gears and/or actuators in the tool housing 204 can control the operation of various features associated with the tool's end effector (e.g., clamping, firing, rotation, articulation, energy delivery, forcing to an unarticulated position, etc.), as well as control the movement of the shaft 202 (e.g., rotation of the shaft). The shaft 202 can include actuators and connectors that are operatively coupled to the gears and/or actuators in the tool housing 204 and that extend along the shaft 202 to assist with controlling the actuation and/or movement of the end effector and/or the shaft 202.

Figure 16:
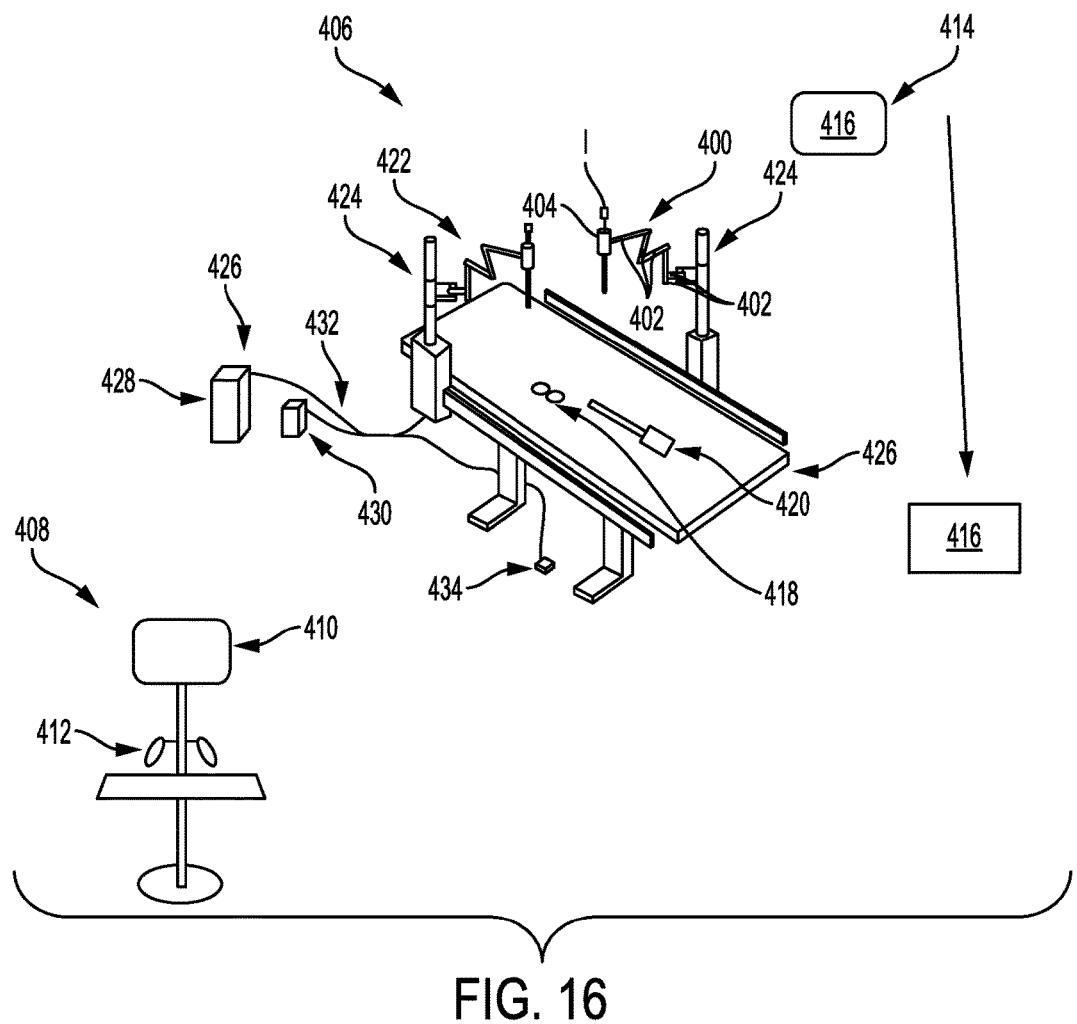
FIG. 16 is a schematic view of one embodiment of a robotic surgical system configured to be operated by a user and to be used during performance of a surgical procedure on a patient.
Figure 17:
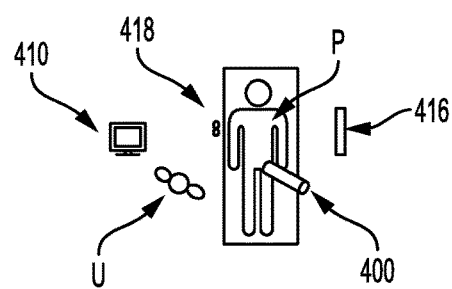
FIG. 17 is a schematic view of one embodiment of the robotic surgical system of FIG. 16 in use during performance of a surgical procedure on a patient.

FIGS. 16 and 17 illustrate one embodiment of a robotic surgical system 406 configured to facilitate performance of a surgical procedure on a patient P and to be releasably coupled to any of the embodiments of surgical tool disclosed herein. The robotic surgical system 406 includes an arm 400 in the form of an electromechanical arm. The electromechanical arm 400 includes one or more mechanical members 402 configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.). The arm 400 also includes a plurality of joints between adjacent mechanical members 402, and a coupling mechanism 404 configured to removably and replaceably couple to a surgical instrument I that can include one of the surgical tools disclosed herein. The arm 400 includes five mechanical members 402 and four joints in this illustrated embodiment, but arms can have any number of mechanical members and associated joints.

Figure 18:
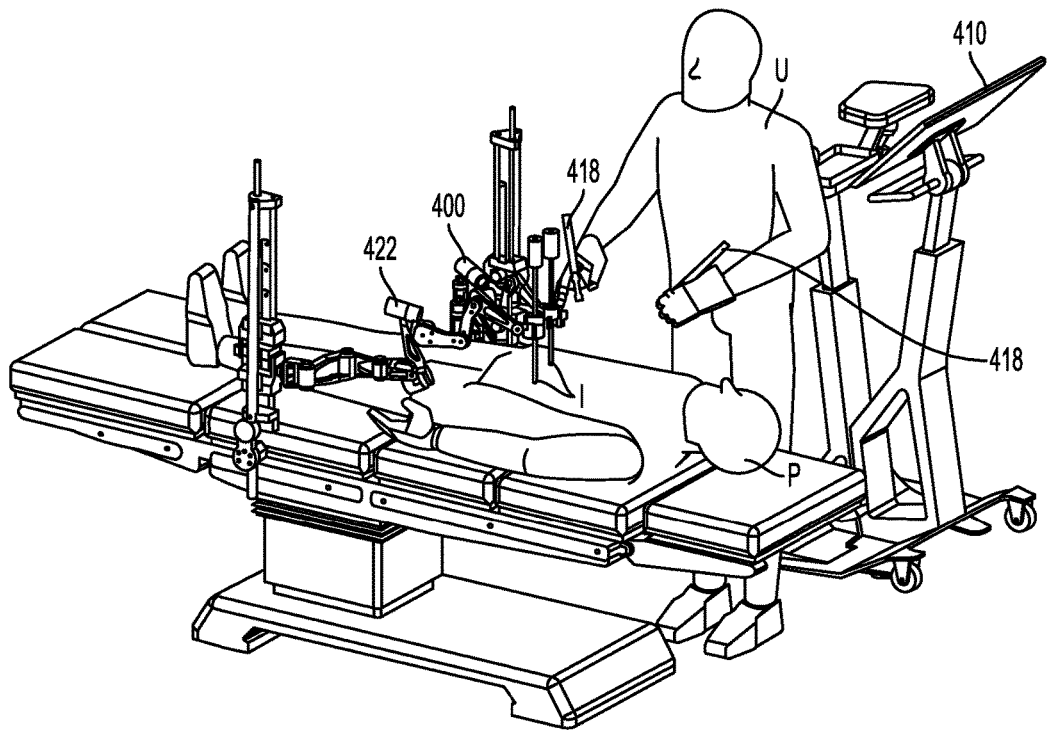
FIG. 18 is a perspective view of the robotic surgical system of FIG. 7 in use during performance of the surgical procedure on a patient.

FIG. 18 shows one embodiment of the system 406 in use. The system 406 includes a user interface sub-system 408 that includes at least one display 410 configured to display information thereon to a user U, at least one user input device 412 configured to receive a user input thereto to control movement of the arm 400, a visualization system 414 that includes at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arm 422 configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 includes at least one computer system 428, one or more cables 432, and at least one power supply 430. The computer system 428 includes at least one processor (not shown). At least some embodiments of control systems can be at least partially wireless, in which case at least some of the cables 432 need not be present. The robotic surgical system 406 includes at least one foot pedal 434 coupled to the computer system 428 via one of the cables 432, which can allow the foot pedal 434 to serve as a user input device. The robotic surgical system 406 can include at least one knee control (not shown) coupled to the computer 428 via one of the cables 432, similar to a knee control of a sewing machine, which can allow the knee control to serve as a user input device.

The robotic surgical system 406 includes a frame 424 for each of the arms 400, 422. The frames 424 in this illustrated embodiment are each mounted to a surgical table 426, but the frames 424 can be mounted elsewhere. The frames 424 in this illustrated embodiment include a vertical extension movably coupled to a rail mounted to the table 426. The vertical extension is configured to move along the rail, thereby facilitating positioning of the arms 400, 422 relative to the patient P.

One or more manually operated surgical instruments 420, e.g., instruments not under the control of the robotic surgical system 406, are also being used to perform the surgical procedure being performed on the patient P. In other embodiments, no manual instruments 420 are used.

Aspects of the robotic surgical system 406 are further described in previously mentioned International Patent Publication No. WO 2014/151621 entitled "Hyperdexterous Surgical System" filed on Mar. 13, 2014.

The systems, devices, and methods disclosed herein can be implemented using one or more computer systems. One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer system having a display device, such as for example a cathode ray tube (CRT) or a liquid crystal display (LCD) or a light emitting diode (LED) monitor for displaying information to the user and a keyboard and an input device, e.g., a mouse, a trackball, a hand tracker, a gesture recognition device (e.g., Kinect), etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 19:
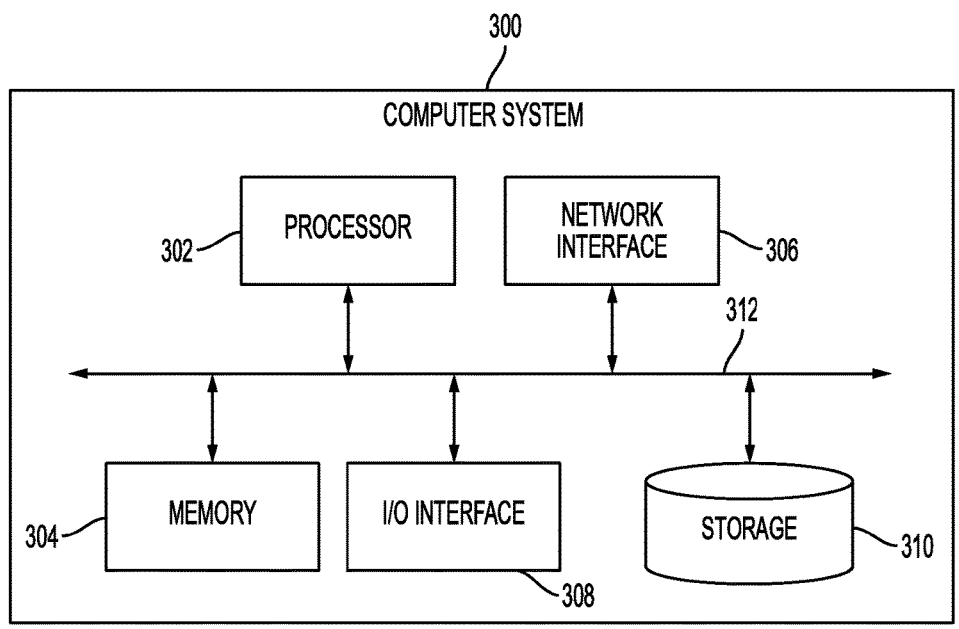
FIG. 19 is a schematic view of one embodiment of a computer system.

FIG. 19 illustrates one exemplary embodiment of a computer system 300. As shown, the computer system 300 can include one or more processors 302 which can control the operation of the computer system 300. "Processors" are also referred to herein as "controllers." The processor(s) 302 can include any type of microprocessor or central processing unit (CPU), including programmable general-purpose or special-purpose microprocessors and/or any one of a variety of proprietary or commercially available single or multi-processor systems. The computer system 300 can also include one or more memories 304, which can provide temporary storage for code to be executed by the processor(s) 302 or for data acquired from one or more users, storage devices, and/or databases. The memory 304 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 300 can be coupled to a bus system 312. The illustrated bus system 312 is an abstraction that represents any one or more separate physical busses, communication lines/interfaces, and/or multi-drop or point-to-point connections, connected by appropriate bridges, adapters, and/or controllers. The computer system 300 can also include one or more network interface(s) 306, one or more input/output (TO) interface(s) 308, and one or more storage device(s) 310.

The network interface(s) 306 can enable the computer system 300 to communicate with remote devices, e.g., other computer systems, over a network, and can be, for non-limiting example, remote desktop connection interfaces, Ethernet adapters, and/or other local area network (LAN) adapters. The IO interface(s) 308 can include one or more interface components to connect the computer system 300 with other electronic equipment. For non-limiting example, the IO interface(s) 308 can include high speed data ports, such as universal serial bus (USB) ports, 1394 ports, Wi-Fi, Bluetooth, etc. Additionally, the computer system 300 can be accessible to a human user, and thus the IO interface(s) 308 can include displays, speakers, keyboards, pointing devices, and/or various other video, audio, or alphanumeric interfaces. The storage device(s) 310 can include any conventional medium for storing data in a non-volatile and/or non-transient manner. The storage device(s) 310 can thus hold data and/or instructions in a persistent state, i.e., the value is retained despite interruption of power to the computer system 300. The storage device(s) 310 can include one or more hard disk drives, flash drives, USB drives, optical drives, various media cards, diskettes, compact discs, and/or any combination thereof and can be directly connected to the computer system 300 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 19 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 300 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 300 can also include a web server for generating and/or delivering the web pages to client computer systems.

In an exemplary embodiment, the computer system 300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
a tool shaft;
an end effector coupled to a distal end of the tool shaft;
a multi-axial wrist disposed between the tool shaft and the end effector, the multi-axial wrist including a plurality of joints;
a plurality of flexible cables extending along the tool shaft and operatively coupled to the end effector such that tension selectively applied to one or more of the plurality of flexible cables causes at least one of pitch and yaw motion of the end effector; and
a homing rod configured to be selectively moveable relative to the end effector from a position in which a distal end of the homing rod is located proximal to the wrist to a position which forces the end effector into a substantially zero-angle position relative to the tool shaft and in which the distal end of the homing rod is not located proximal to the wrist, wherein the end effector includes first and second jaws, and the homing rod is configured to extend into a recess formed in the first jaw.

2. The tool of claim 1, wherein the homing rod is configured to extend through a bore in the multi-axial wrist to prevent motion of the multi-axial wrist.

3. The tool of claim 1, wherein the plurality of flexible cables are configured to move the first and second jaws between open and closed positions.

4. The tool of claim 1, further comprising a housing coupled to a proximal end of the tool shaft, the housing being configured to couple to a driver of a surgical robot such that the driver can control movement of the plurality of flexible cables.

5. The tool of claim 1, wherein the homing rod forcing the end effector in the substantially zero-angle position prevents the end effector from moving from the substantially zero-angle position to a non-zero angle position.

6. The tool of claim 1, further comprising a plurality of sensors configured to sense a position of each of the plurality of flexible cables when the end effector is in the substantially zero-angle position.

7. The tool of claim 1, wherein tension selectively applied to one or more of the plurality of flexible cables causes opening and closing of the jaws, and the homing rod forcing the end effector into the substantially zero-angle position prevents the opening of the jaws.

8. A surgical system, comprising:
the surgical tool of claim 6;
a memory; and
a controller configured to cause the sensed position of each of the plurality of flexible cables to be stored in the memory.

9. The system of claim 8, wherein the controller is configured to receive a user-initiated input requesting movement of the end effector relative to the tool shaft and to cause the requested movement by causing one or more of the plurality of flexible cables to move relative to the tool shaft with reference to the stored sensed position of each of the plurality of flexible cables.

10. The system of claim 8, wherein the controller is configured to cause the plurality of flexible cables to be tensioned prior to the sensing of the position of each of the plurality of flexible cables, the plurality of sensors sensing the position of each of the plurality of flexible cables when the plurality of flexible cables are tensioned.

11. A surgical tool, comprising:
a tool shaft;
an end effector coupled to a distal end of the tool shaft;
a multi-axial wrist disposed between the tool shaft and the end effector, the multi-axial wrist including a plurality of joints;
a plurality of flexible cables extending along the tool shaft and operatively coupled to the end effector such that tension selectively applied to one or more of the plurality of flexible cables causes at least one of pitch and yaw motion of the end effector; and
a homing rod configured to be selectively moveable relative to the end effector from a position in which a distal end of the homing rod is located proximal to the wrist to a position which forces the end effector into a substantially zero-angle position relative to the tool shaft and in which the distal end of the homing rod is not located proximal to the wrist, wherein the end effector includes first and second jaws, and the homing rod includes first and second rods, the first rod being configured to extend into a first recess formed in the first jaw, and the second rod being configured to extend into a second recess formed in the second jaw.

12. A surgical tool, comprising:
a housing configured to couple to at least one motor on a tool driver of a surgical robot;
an elongate shaft extending from the housing;
an end effector coupled to a distal end of the elongate shaft and pivotally movable about at least one pivot joint formed between the end effector and the elongate shaft;
a plurality of flexible cables coupled to the housing, extending along the elongate shaft, and operatively coupled to the end effector, wherein proximal movement of the plurality of flexible cables is effective to cause pivotal movement of at least a portion of the end effector relative to the elongate shaft about the at least one pivot joint; and
a rigid member operably associated with the end effector and configured to be selectively advanced into a recess formed in the end effector to prevent the end effector from pivoting about the at least one pivot joint, wherein the rigid member is configured to be selectively advanced into the recess from a first position, in which a distal end of the rigid member is located proximal to the at least one pivot joint, to a second position, in which the distal end of the rigid member is not located proximal to the at least one pivot joint.

13. The tool of claim 12, further comprising a first actuator configured to be actuated to advance the rigid member into the end effector.

14. The tool of claim 12, wherein each of the plurality of flexible cables is configured to move proximally relative to the elongate shaft to pivot the end effector relative to the elongate shaft, and the rigid member is configured to move distally relative to the elongate shaft to force the substantial longitudinal alignment of the end effector with the elongate shaft.

15. The tool of claim 12, wherein the end effector includes a pair of jaws, and the plurality of flexible cables are configured to move relative to the elongate shaft to selectively open and close the pair of jaws.

16. The tool of claim 15, wherein the rigid member includes a pair of rigid members, each of the rigid members being configured to be advanced into one of the jaws.

17. The tool of claim 12, wherein the end effector includes one of forceps, graspers, a needle driver, scissors, an electrocautery tool, a stapler, a clip applier, a suction tool, and an irrigation tool.

18. The tool of claim 12, further comprising a plurality of sensors configured to sense a position of each of the plurality of flexible cables when the rigid member is advanced into the end effector and the end effector is substantially longitudinally aligned with the elongate shaft.

19. The tool of claim 18, wherein the surgical robot includes a memory and a controller, the controller being configured to cause the sensed position of each of the plurality of flexible cables to be stored in the memory.

20. The tool of claim 12, wherein the end effector includes a pair of jaws, and the recess is formed in a proximal end of at least one of the jaws.

21. The tool of claim 12, wherein the at least one pivot joint includes a multi-axial wrist disposed between the shaft and the end effector, the rigid member configured to be selectively advanced from the first position in which the distal end of the rigid member is located proximal to the multi-axial wrist.

* * * * *